(12) United States Patent
Järverud

(10) Patent No.: US 7,082,329 B2
(45) Date of Patent: Jul. 25, 2006

(54) METHOD AND MONITOR FOR MONITORING DIASTOLIC RELAXATION OF A HEART VENTRICLE

(75) Inventor: Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 494 days.

(21) Appl. No.: 10/432,970

(22) PCT Filed: Nov. 26, 2001

(86) PCT No.: PCT/SE01/02615

§ 371 (c)(1), (2), (4) Date: May 28, 2003

(87) PCT Pub. No.: WO02/43587

PCT Pub. Date: Jun. 6, 2002

(65) Prior Publication Data
US 2004/0049238 A1    Mar. 11, 2004

(30) Foreign Application Priority Data
Nov. 28, 2000    (SE) .................................... 0004417

(51) Int. Cl.
*A61N 1/365* (2006.01)

(52) U.S. Cl. ............................. 607/17; 607/9; 607/62; 600/547

(58) Field of Classification Search ................ 600/508, 600/513, 523, 547; 607/9, 17, 18, 62
See application file for complete search history.

(56) References Cited

U.S. PATENT DOCUMENTS

| 4,095,705 A | * | 6/1978 | Hood .......................... 414/519 |
| 4,905,696 A | | 3/1990 | Amundson et al. |
| 5,211,177 A | | 5/1993 | Chesney et al. |
| 5,427,112 A | | 6/1995 | Noren et al. |
| 5,556,419 A | | 9/1996 | Jarverud et al. |
| 5,735,286 A | * | 4/1998 | Notton et al. ................ 600/513 |

FOREIGN PATENT DOCUMENTS

| EP | 0 607 511 | 7/1994 |
| EP | 0 615 770 | 9/1994 |

OTHER PUBLICATIONS

"Usefulness of the Impedance Cardiogram to Reflect Left Ventricular Diastolic Function," Pickett et al., The American Journal of Cardiology, vol. 71, May 1, 1993, pp. 1099-1103.
An Abnormal Early Diastolic Impedance Waveform: A Predictor of Poor Prognosis in the Cardiac Patient, Ramos, American Heart Journal, vol. 94, No. 3, (Sep. 1977) pp. 274-281.

* cited by examiner

*Primary Examiner*—Robert E. Pezzuto
*Assistant Examiner*—Yun H. Lee
(74) *Attorney, Agent, or Firm*—Schiff Hardin LLP

(57) ABSTRACT

In a monitor for monitoring diastolic relaxation of a ventricle of a heart, an impedance signal is measured in a ventricle of the heart and the occurrence of a notch in the impedance signal coincident with the entry of blood into the monitored ventricle is detected by forming a time derivative of the impedance signal and generating a loop by plotting impedance values of the impedance signals with respect to related time derivative values to form a loop for each cardiac cycle of the heart, and comparing the generated loop to a loop template representing a normal loop for the subject, to identify deviations in the loop from normal deviations in timing and shape of the notch.

13 Claims, 10 Drawing Sheets

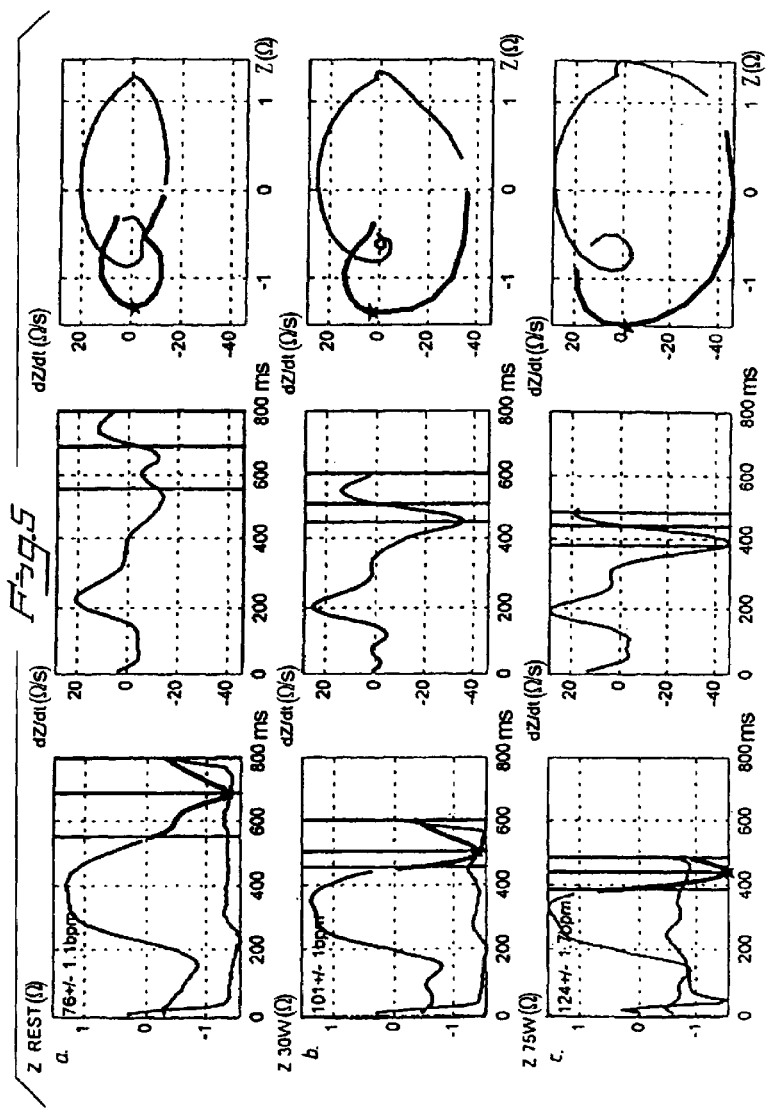

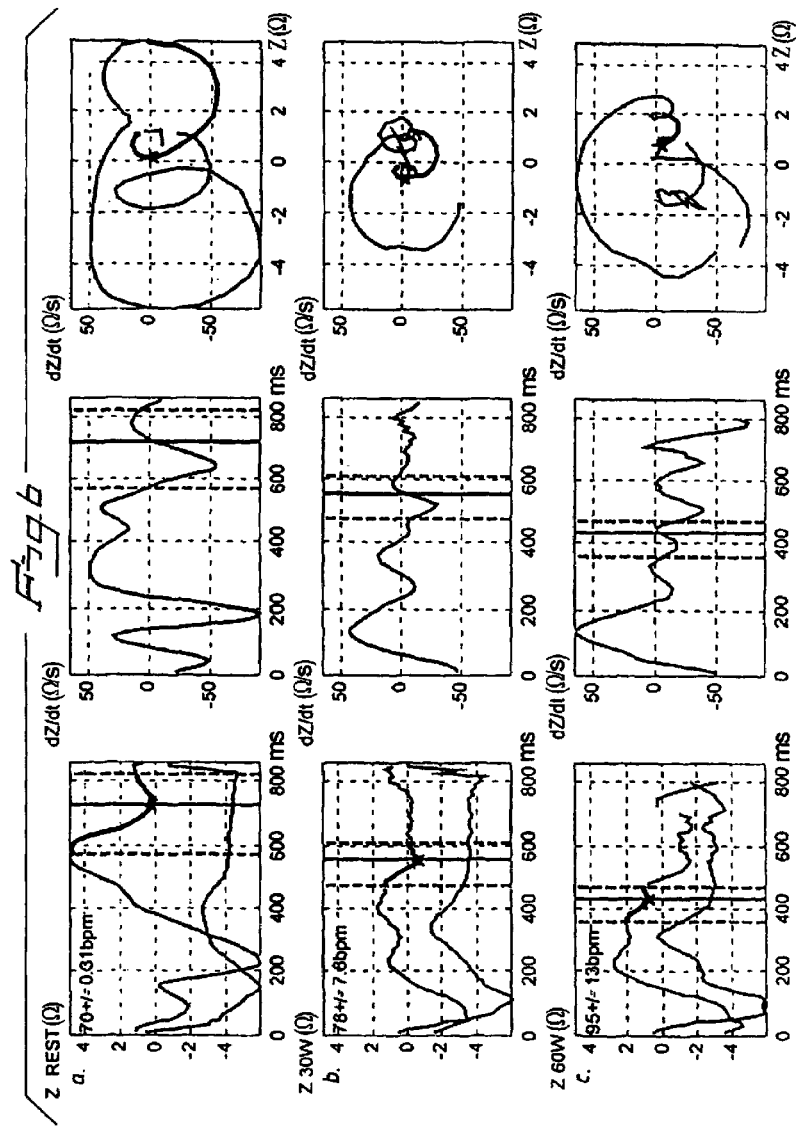

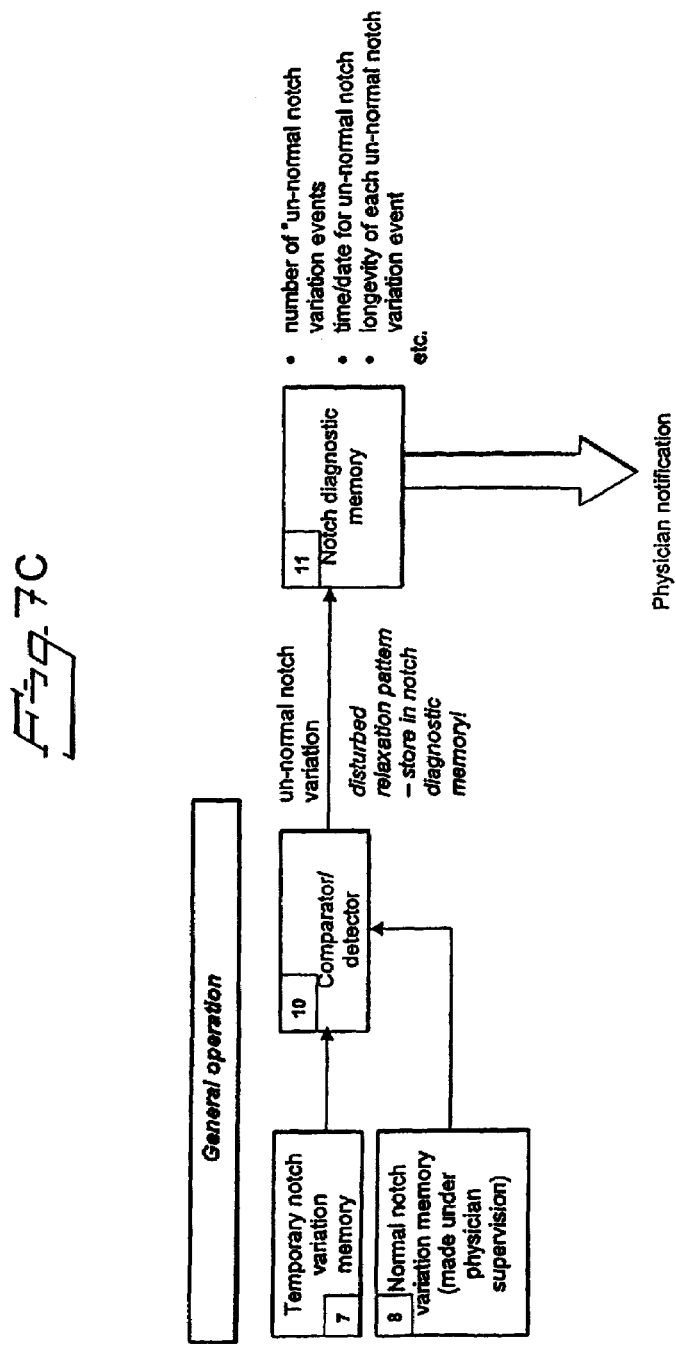

ent METHOD AND MONITOR FOR
MONITORING DIASTOLIC RELAXATION
OF A HEART VENTRICLE

TECHNICAL FIELD

The present invention relates to a monitor for monitoring diastolic relaxation of at least one ventricle of a patients heart, comprising an impedance measurement means including electrode means for measuring an impedance and generating a corresponding impedance signal, a detecting means connected to said impedance measurement means for detecting the occurance of at least one notch in said impedance signal coincident with the entry of blood into at least one ventricle of the heart and for detecting at least one parameter of said at least one notch. This invention also relates to a method of monitoring diastolic relaxation of a patient's heart comprising the steps of measuring an impedance by means of electrode means adapted for a location significant for one or both of the lower chambers of the heart or for location in coronary sinus, generating a corresponding impedance signal, and detecting at least one notch coincident with the entry of blood into at least one of said chambers.

BACKGROUND

Congestive heart failure is a fast growing health problem that mostly affects older adults. In this condition the heart is unable to pump enough blood to meet the needs of the body's organs. Among the most common causes of congestive heart failure can be mentioned coronary artery disease, causing myocardial ischemia, myocardial infarction and cardiomyopathy. During ischemia the cardiac relaxation, i.e. diastole, is changed or disturbed because the cardiac muscle is stiffened. A disturbed diastolic phase or diastolic failure is a very early sign of congestive heart failure, such that at this early stage it might not even appear as symptoms to the patient. If it would be possible to detect these early signs of disturbed relaxation patterns, the physician would be capable of taking actions preventing congestive heart failure to escalate which often will result in reduced systolic capacity.

In U.S. Pat. No. 4,905,696 it is described that the P-wave in the electrocardiogram can be detected as a rapid inflection or notch in a ventricular impedance signal. This phenomenon is used for providing P-synchronous heart stimulation of a patient's heart.

It is known that a notch appears in the impedance signal corresponding to early diastole of a cardiac cycle cf. Brian R. Pickett et al., The American Journal of Cardiology, vol. 71, May 1, 1993, "Usefulness of the Impedance Cardiogram to Reflect Left Ventricular Diastolic Function". In this document a study is described of the correlation between a dip in a non-invasively measured impedance and Doppler measurements for diastolic studies.

FIG. 1 shows examples of measurements from animal tests, more precisely results from measurements on a sheep. Curve a shows an impedance signal measured with a standard bipolar pacing lead positioned in right ventricular apex as indicated in the figure. Curves b and c show the right ventricular pressure and the left ventricular pressure respectively. Curve d is the surface ECG and curve e shows the respiratory flow. As appears from the figure, a distinct notch is seen in the intracardiac impedance, marked by a circle in curve a, is seen in the majority of measurements. Its location is closely after the point where the ventricular pressure curves b and c are down to a minimum and prior to atrial systole, i.e. the notches are located in early heart diastole. In some measurements the notch occurs at the time of atrial systole which could lead to the conclusion that it is caused by atrial contraction. However, the notch is present even if no atrial activity is observed, i.e. even when no P-wave is available.

The impedance measured in human beings also exhibits a notch, marked by circles in FIG. 2, cf. also the above-mentioned document by Brian R. Pickett et. al. The diagrams a in FIG. 2 show the bipolar right ventricular impedance measured in humans with no prior history of coronary artery decease for three different tip-ring distances, viz 10, 20 and 30 mm respectively. Corresponding intracardiac ECGs are shown at b in the figure. The measurements shown in FIG. 2 are made during rest conditions with the patient lying down, and the curves shown are calculated from measurements during 10 or more heartbeats. As appears a distinct notch in the diastolic impedance is shown in all examples, and this notch is occurring after the end of the T-wave in the ECG, marking the start of relaxation or diastole, and before the appearance of the subsequent P-wave.

FIG. 3 shows another example of such bipolar right ventricular impedance measurements on a human being during rest conditions and drug-induced workload together with corresponding ECGs. Also in this case the curves shown are averaged curves of both the intracardiac electrogram and the impedance calculated from 10 or more heartbeats. A distinct notch in diastolic impedance is seen in all examples, marked by circles in the figure. Although the over-all impedance might show a slight change in morphology, little or no change in notch appearance between rest and load conditions is observed, the timing of the notch being earlier during load. Thus for a healthy patient the shape of the notch does not change significantly with the load, whereas the situation might be different for patients with cardiac abnormalities that alter the relaxation patterns.

FIG. 4 shows the right ventricular bipolar impedance i), the first time derivative of the impedance ii), and a corresponding loop plot iii) of these two signals. As appears there is very little variation in the impedance notch appearance. The three set of diagrams i, ii and iii, represent three different tip-ring distances, viz. 10 mm, 20 mm and 30 mm respectively.

To use such loops, formed by plotting parameter values against related time derivative values, as an aid for analysis of phenomena and functions of the heart is previously described in e.g. U.S. Pat. Nos. 5,427,112 and 5,556,419.

In FIG. 5 the unipolar impedance, i.e. the impedance measured between an electrode tip positioned in the ventricular apex and the casing of the implanted monitor is shown together with the corresponding time derivative of this impedance signal and the loop plot for a healthy patient in rest, curve a, for a load of 30 W, curve b, and a load of 75 W, curve c. Also in this case the occurrence of the notch in the impedance signal is evident.

FIG. 6 shows results from corresponding measurements on a patient with dilated cardiomyopathy. The curves a), b) and c) show the result from right ventricular unipolar impedance measurements in a patient during rest, curve a, a load of 30 W (cycling), curve b and a load of 60 W (cycling), curve c. The impedance signal Z, the first time derivative of the impedance dZ/dt and a loop plotted of these two signals dZ/dt and Z are shown. In these examples there is a marked change in the impedance notch appearance between rest and load situations, which is related to relaxation disturbances of the patient. The changes in the notch appearance are emphasized in the loop plots.

Animal tests comprising impedance measurements performed simultaneously with echocardiographic measurements of mitral blood flow also show the appearance of an impedance notch at the time for maximum inflow in early diastole, and prior to the ventricular filling caused by atrial contraction. It has also appeared that the time between ECG R-wave and the occurrence of an impedance notch correlate well with the heart rate in a physiological manner.

To sum up, tests show that the notch appearing in the diastolic impedance is related to a ventricular event, and not to an atrial event. In practically all tests the notches occur prior to atrial systole. In some cases the time interval between the T-wave in one heartbeat and the P-wave in the subsequent beat is short and in such cases the notch can be seen to occur simultaneously with the electrical P-wave, however, echocardiographic measurements of mitral blood flow show, as mentioned above, that the atrial contribution to ventricular filling occurs after the impedance notch, i.e. the notch is related to rapid ventricular filling in early diastole.

DISCLOSURE OF THE INVENTION

The purpose of the present invention is to utilize the above discussed knowledge to provide a notch monitoring diagnostics for detecting early signs of disturbed relaxation patterns of the heart.

This purpose is obtained by a monitor, and a method according to the introductory portion having the characterizing features of claim 1 and 14 respectively.

Thus in the present invention any change, other than normal notch variations, in the parameter considered indicates a relaxation disturbance. Said parameter is compared to a template defining normal notch variations, i.e. timing and shape, during for example rest and workload, upright and supine position etc. An example of such normal changes in notch characteristics is a reduced time interval between R-wave, or ventricular stimulation, and detected notch with increased heart rate, as discussed above. For this purpose the loop is superior to e.g. signal-to-time representation since it does not only take the signal of interest into account, but also one additional quantity is analysed. Small changes in the measured signal are revealed in this way in much greater detail. The template must be determined for each individual patient under the supervision of a physician. The monitoring possibility of early signs of disturbed relaxation patterns obtained by the present invention give a very important diagnostic advantage and make it possible for the physician to take suitable actions that would prevent a congestive heart failure to escalate and perhaps even prevent the patient from hospitalization.

According to an advantageous embodiment of the monitor according to the invention, wherein said monitor comprises means to supervise the patient's heart rate, said comparator is adapted to determine the correlation between the time between the apperance of an R-wave/ventricular stimulation and the time of the notch occurrence, and the heart rate. The detecting means is preferably adapted to detect the timing of occurred notches by measuring the time between the appearance of R-wave or, where appropriate, the delivery of a ventricular stimulation pulse, and subsequent occurrence of a notch in the impedance signal. Thus the time interval between sensed R-wave or ventricular stimulation event, and detected notch is measured and can be stored together with actual heart rate to make it possible for the physician to follow notch behavioural statistics in terms of date and time for notch change, number of notch change events, frequency change and longevity, level of notch change etc. for then deciding whether to make additional medical check-ups.

According to another advantageous embodiment of the monitor according to the invention said comparator is adapted to compare the shape of the loop in that part of the loop which corresponds to the notch portion of the impedance signal with corresponding part of the loop template. Certain phenomena appearing in the impedance signal can be emphasized in the loop plot, thus facilitating detection and analysis of these phenomena.

According to still another advantageous embodiment of the monitor according to the invention said comparator is adapted to compare notch timing and shape, notch time derivatives and corresponding loop characteristics with corresponding predetermined timing and shape, time derivative and loop templates respectively. By simultaneously studying the three quantities impedance signal, time derivative of the impedance signal and the loop obtained from values of impedance signal and its time derivative a still more reliable detection of possible disturbances in the diastolic relaxation pattern can be detected.

According to yet other advantageous embodiments of the monitor according to the invention a first averaging means is connected to said impedance measuring means for determining an average impedance signal of impedance signals measured during a predetermined number of cardiac cycles and said detecting means is connected to said first averaging means to detect the occurrence of and said parameter of said at least one notch from said average impedance signal. By using average signals in this way the reliability in the detection of disturbances in the diastolic relaxation can be still improved.

In some cases the notch may, however, appear somewhat unclear and not distinct in the average impedance signal. The notch may in these cases appear more clearly in the standard deviation curve obtained from the measured impedance curves. Therefore, according to another advantageous embodiment of the monitor according to the invention said first averaging means is adapted to determine the standard deviation of impedance signals measured during a predetermined number of cardiac cycles and said detecting means is connected to said first averaging means to detect the occurrence of and said parameter of said at least one notch from said standard deviation.

The invention also relates to a heart stimulator comprising a pulse generator for generating stimulation pulses for delivery to a patient's heart by means of electrode means adapted for location in one or both of the lower chambers of the heart, which is characterized by a monitor according to the invention. By providing a heart stimulator with such a notch monitoring diagnostics a heart stimulator is obtained having much improved diagnostic possibilities.

The invention also relates to a method of monitoring diastolic relaxation of a patient's heart according to the introductory portion of the description, which is characterized by the steps of forming the time derivative of the impedance signal, plotting impedance values against related time derivative values to form a loop for each cardiac cycle, and comparing said loop with a predetermined loop template. Thus according to the invention an impedance signal can be used which is obtained by means of electrode means located in one or both of the lower chambers of the heart or in coronary sinus.

BRIEF DESCRIPTION OF THE DRAWINGS

To explain the invention in greater details an embodiment of the monitor according to the invention will be described in the following with reference to FIGS. 7–9 of the drawings, on which FIG. 5 shows an unipolar impedance signal obtained from a healthy patient for rest condition and two different load conditions together with corresponding time derivatives and loops, FIG. 6 shows the corresponding curves for a cardiomyopathy patient.

DESCRIPTION OF A PREFERRED EMBODIMENT

Figure 1:
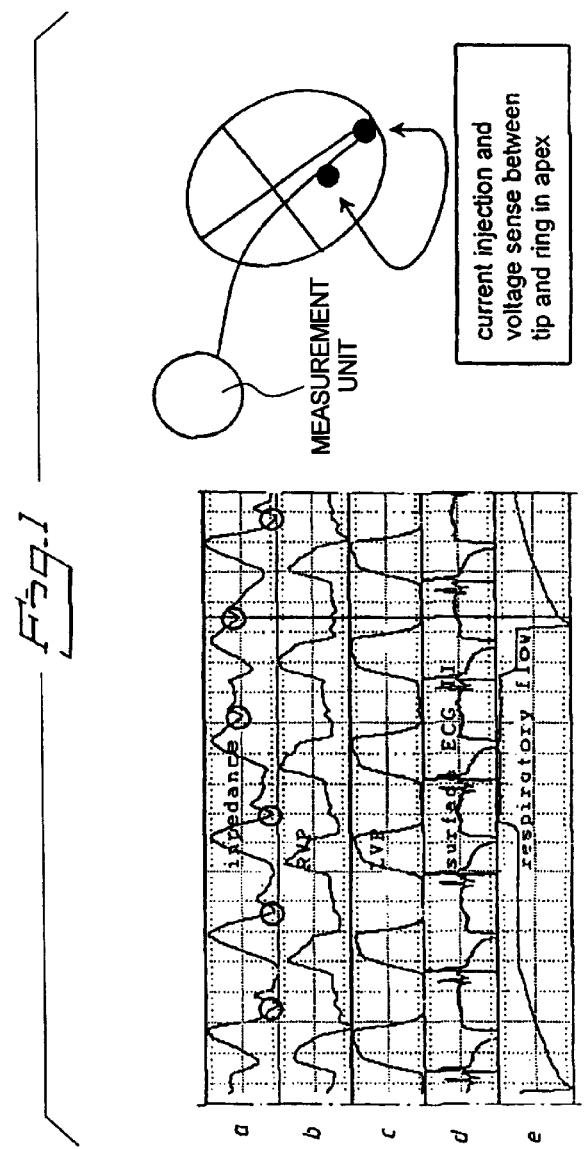
FIG. 1 shows measurement signals obtained from an animal test.
Figure 2:
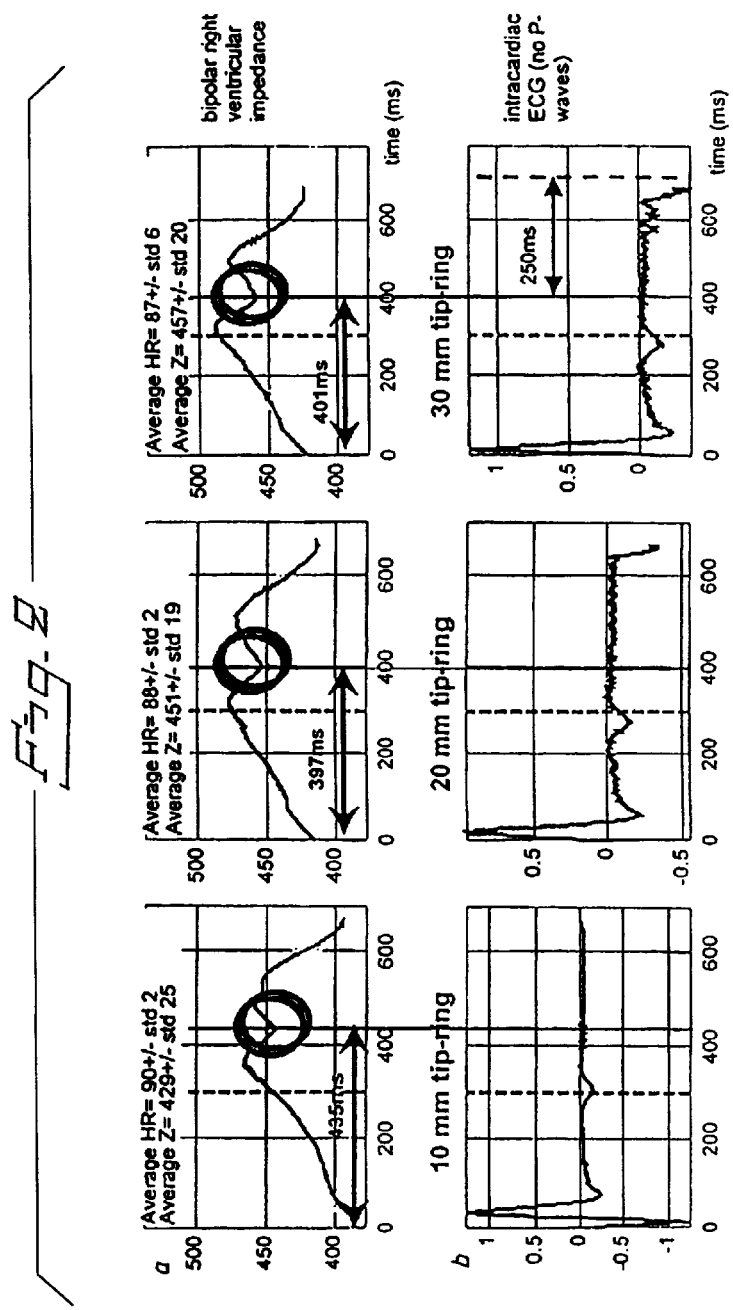
FIGS. 2 and 3 show the impedance signal and intercardiac ECG obtained from a human being during rest condition and during drug-induced workload.
Figure 3:
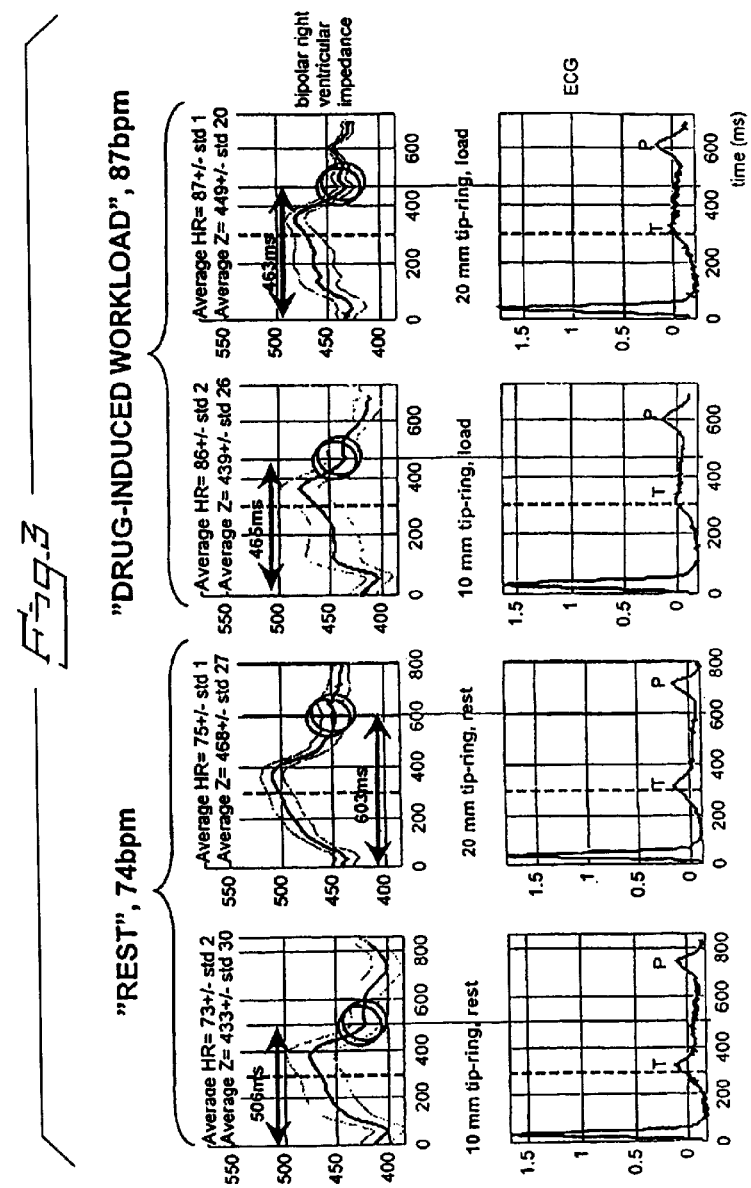
Figure 4:
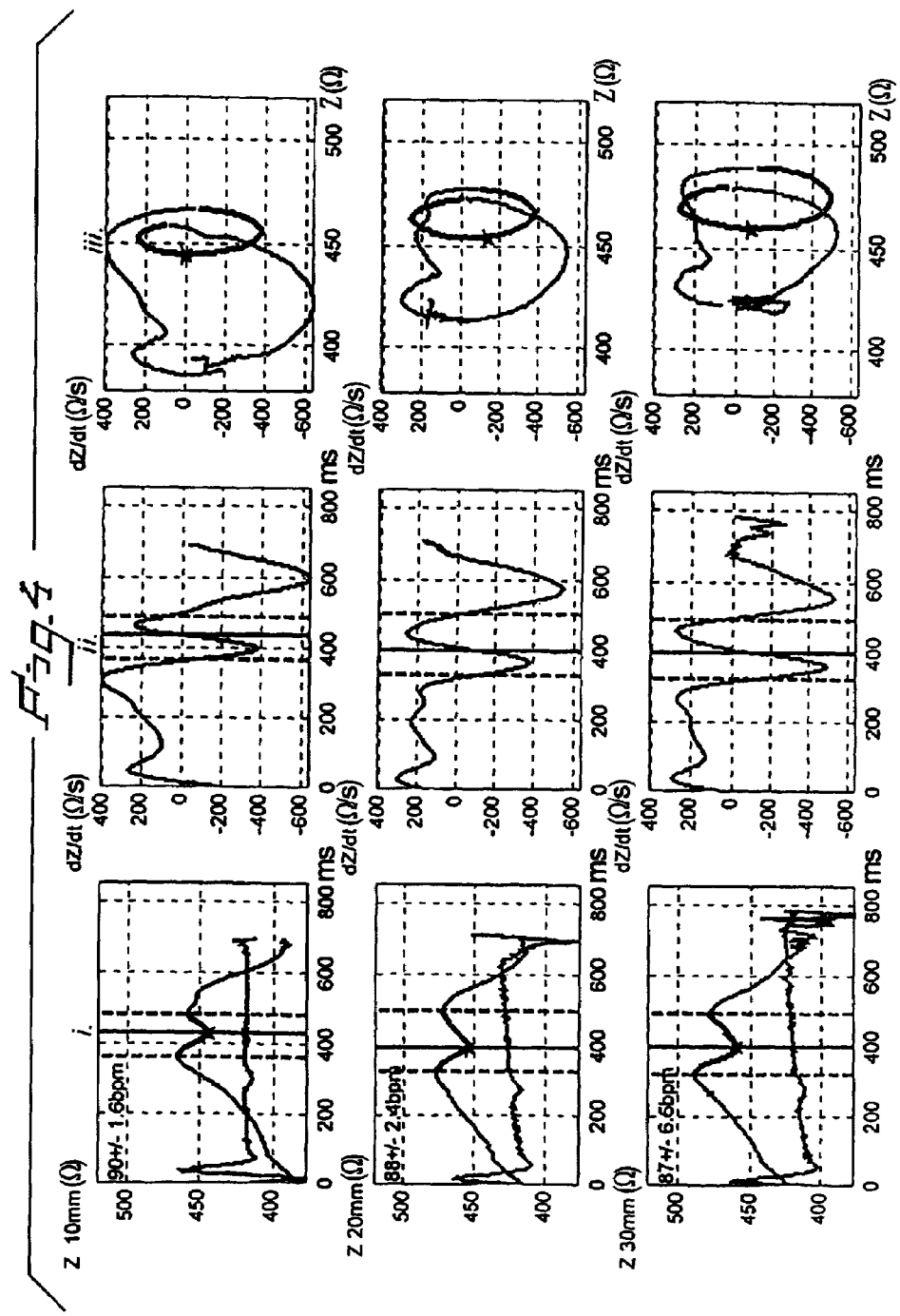
FIG. 4 shows the impedance signal, the time derivated impedance signal and corresponding loops formed by impedance values and corresponding time derivatived values from right ventricular bipolar impedance measurements in a healthy patient during rest for three different interelectrode distances.
Figure 7A:
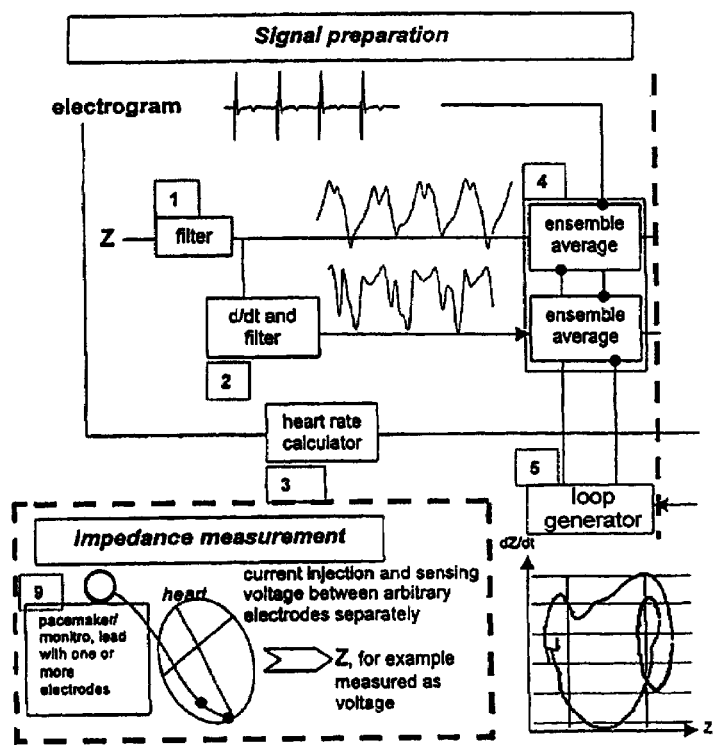
FIG. 7 shows in the form of a blockdiagram an embodiment of the monitor according to the invention.
Figure 7B:
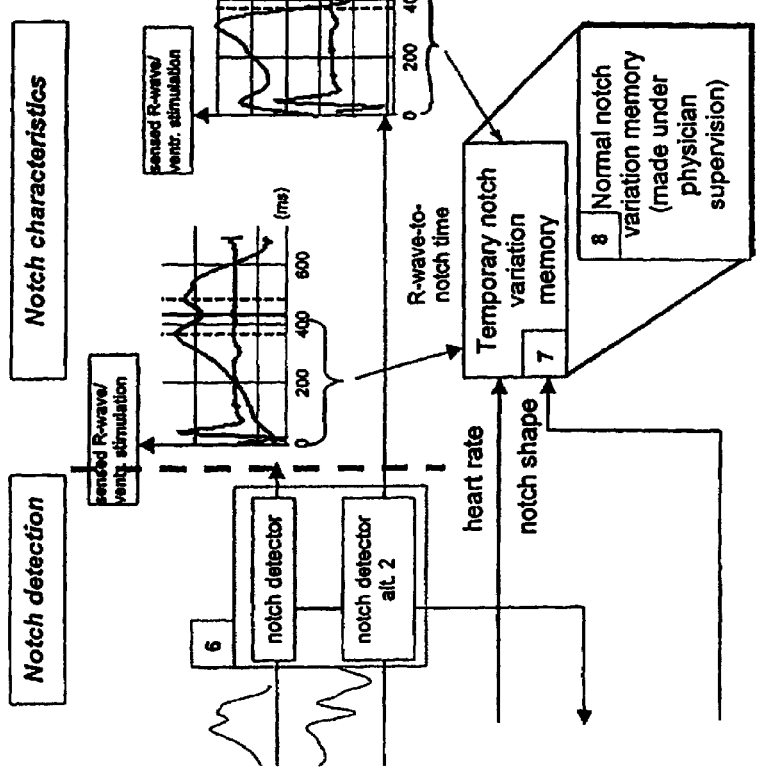

The blockdiagram in FIG. 7 is divided into a signal preparation part, a notch detection part, a notch characteristics part, an impedance measurement part, and a final general operation part.

The letter Z denotes the measured impedance, as will be further explained below, and in the signal preparation part the impedance signal Z is supplied to a filter 1, which is a smoothing filter for the raw impedance signal in order to remove noise and artefacts. The time derivative and filter unit 2 is a high pass filter to create a first time derivate of the impedance signal and a smoothing filter to remove noise and artefacts An electrogram is also recorded for the patient and supplied to a heart rate calculator 3. The heart rate calculator calculates the heart rate from sensed R-waves, or where appropriate, ventricular stimulations.

An ensemble average unit 4 is provided to calculate an average impedance signal from e.g. ten cardiac cycles, as measured from the electrogram. The ensemble average unit 4 is adapted to also calculate a corresponding averaged time derivative.

A loop creator 5 is connected to the ensemble average unit 4 to receive the average impedance signal and the average time derivative and form a loop for the cardiac cycle by plotting impedance values against related time derivative values. From the loop together with timing inputs from a notch detector 6 notch characteristics are determined.

The notch detector 6 of the notch detection part is connected to the ensemble average unit 4 to detect the existence of notches from the average impedance signal and, if so, the timing in the cardiac cycle of the notch. The notch detector 6 is adapted to determine, as an alternative, the existence of a notch from the average time derivative received from the ensemble average unit 4.

In the temporary notch variation memory 7 of the notch characteristics part notch characteristics, for example notch shapes as seen in either impedance signal, first time derivative of the impedance signal or in the corresponding loop, R-wave to notch time correlated to heart rate, etc. are continuously stored.

The normal notch 8 variation memory contains normal notch variation pattern templates for the characteristics stored in memory 7. These templates are unique for each patient and are individually determined under the supervision of a physician.

The impedance measurement part illustrates the impedance measurements performed by the monitor according to the invention or by a heart stimulator, like a pacemaker, provided with such a monitor. The monitor or heart stimulator comprises a lead with one or more electrodes, in the example a bipolar ventricular electrode is shown. Current is supplied through the lead and the corresponding voltage between the two electrodes or between one electrode and the monitor or stimulator casing is measured. This voltage represents the impedance Z.

The final general operation part of the monitor (or stimulator) includes a comparator and detector 10 for continuos comparison of actual notch variation pattern, received from the memory 7, with a template, received from the memory 8. By this comparator and detector 10 any abnormal notch pattern is detected, like loss of notches and change in notch shape, as seen in the corresponding loop, as well as discrepancies in the R-wave to notch time correlation to heart rate, etc.

Notch pattern variations including any detection of abnormal notch variation patterns are stored in the notch diagnostic memory 11. Thus e.g. the number of abnormal notch variation events, time and date for abnormal notches, longevity of each abnormal notch variation event, level of notch changes etc. can be stored. The physician can then use this information to follow notch behavioural statistics to decide whether to make additional medical check-ups.

Figure 8:
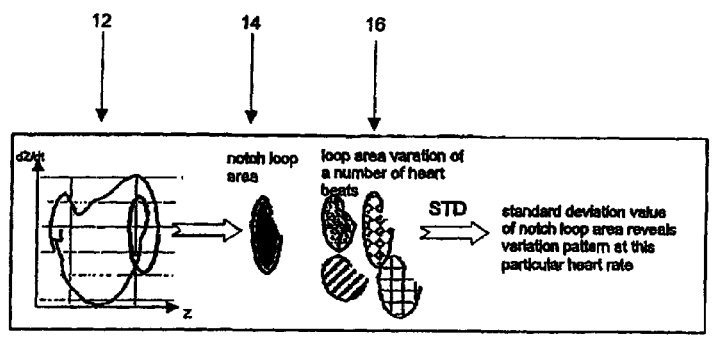
FIG. 8 illustrates an example of obtaining information about notch pattern variation.

FIG. 8 illustrates an example of obtaining information about notch pattern variations. At 12 a dZ/dt-Z loop from one heartbeat is shown, and at 14 the corresponding notch loop area is shown. At 16 in FIG. 8 notch loop areas from a plurality of heartbeats are shown. As appears the loop areas obtained from different heartbeats vary and the standard deviation value STD of the notch loop areas reveals the variation pattern at this particular heart rate.

Figure 9:
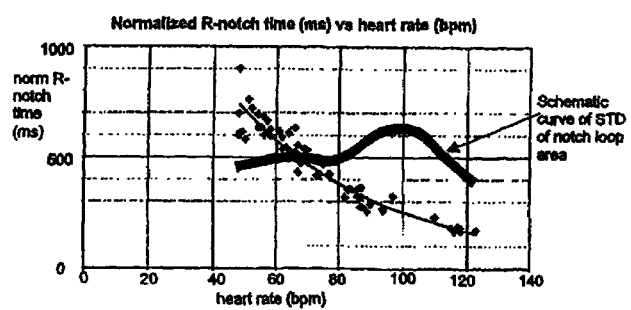
FIG. 9 shows the R-wave-notch time and the standard derivation of the notch loop area as functions of the heart rate.

FIG. 9 shows an example of measured normalized R-wave-notch time plotted against heart rate (bpm). This is what it might look like in one single patient. Along with the measured temporal information, a schematic curve of standard deviation STD of the notch loop area is plotted against the heart rate. Together these curves form one example of notch variation pattern that can be calculated and then stored in the temporary notch variation memory 7 in FIG. 7 and compared to a normal notch variation pattern stored in the memory 8 in FIG. 7.

This is just one example of presenting notch characteristics in terms of variation pattern. It is obvious that several other combinations of quantities can be used to present such notch characteristics.

I claim:

1. A monitor for monitoring diastolic relaxation of a ventricle of a heart comprising:
    an impedance measurement unit, including an electrode arrangement adapted to interact with a monitored ventricle of a heart of a subject to measure an impedance in said monitored ventricle, for generating an impedance signal corresponding to said impedance;

a detector connected to said impedance measurement unit for detecting an occurence of a notch in said impedance signal coincident with entry of blood into said monitored ventricle, said detector comprising a differentiator which forms a time derivative of said impedance signal and a loop generator connected to said impedance measurement unit and to said differentiator for plotting impedance values with respect to related time derivative values to form a loop for each cardiac cycle of said heart; and a comparator connected to said loop generator for comprising said loop in a loop template representing a normal loop for the subject, said comparator generating an output indicative of deviators in said loop from normal variation in timing and shape of said notch.

2. A monitor as claimed in claim 1 for use with a pacing circuit adapted to interact with the subject to produce a paced ventricular stimulation in said monitored ventricle, and wherein said monitor further comprises a detector adapted to interact with the subject to obtain an electrocardiogram indicative of a heart rate of the subject, and wherein said comparator determines a correlation between a time between an appearance of one of an R-wave in said electrocardiogram and a ventricular stimulation of said monitored ventricle, and a time of occurence of said notch and said heart rate.

3. A monitor as claimed in claim 1 wherein said comparator compares a shape of said loop, generated by said loop generator, in a region containing said notch with a shape of a corresponding region containing said notch in said loop template.

4. A monitor as claimed in claim 1 wherein said impedance measurement unit measures said impedance in said monitored ventricle over a plurality of cardiac cycles, thereby obtaining a plurality of impedance signals, and wherein said detector comprises an averaging unit for determining an average impedance signal from said plurality of impedance signal as a time derivative of said average impedance signal, and wherein said loop generator plots impedance values of said average impedance signal with respect to related time derivative values of said average impedance signal to form said loop.

5. A monitor as claimed in claim 1 wherein said impedance measurement unit measures an impedance signal in said monitored ventricle over a plurality of cardiac cycles, thereby obtaining a plurality of impedance signals, and wherein said detector comprises a unit for determining a standard deviation curve of said plurality of impedance signals, and wherein said differentiator forms said time derivative of said impedance signal as a time derivative of said standard deviation curve, and wherein said loop generator plots impedance values of said standard deviation curve with respect to related time derivative values of said standard deviation curve to form said loop.

6. A monitor as claimed in claim 1 wherein said impedance measurement unit measures an impedance signal in said monitored ventricle over a plurality of cardiac cycles, thereby obtaining a plurality of impedance signals, and wherein said detector includes a first averaging unit for forming an average impedance signal from said plurality of impedance signals, and wherein said differentiator forms a time derivative of each of said plurality of impedance signals, thereby obtaining a plurality of time derivatives, and wherein said detector comprises a second averaging unit performing an average time derivative from said plurality of time derivatives, and wherein said loop generator plots impedance values from said average impedance signal with respect to related time derivative values from said average time derivative to form said loop.

7. A monitor as claimed in claim 6 wherein said first averaging unit and said second averaging unit comprises a single averaging unit.

8. A monitor as claimed in claim 1 wherein said impedance measurement unit measures impedance in said monitored ventricle over a plurality of cardiac cycles, thereby obtaining a plurality of impedance signals, and wherein said detector comprises a first unit for forming a standard deviation curve of said plurality of impedance signals, and wherein said differentiator forms a time derivative of each of said plurality of impedance signals, thereby obtaining a plurality of time derivatives, and wherein said detector comprises a second unit for forming a standard deviation curve of said plurality of time derivatives, and wherein said loop generator plots values of said standard deviation curve of said plurality of impedance signals with respect to related time deviation values of said standard deviation curve of said plurality of time derivative to form said loop.

9. A monitor as claimed in claim 8 wherein said first unit and said second unit comprises a single unit.

10. A monitor as claimed in claim 1 wherein said impedance measurement unit includes a bipolar ventricle electrode having an electrode tip and an electrode ring adapted for placement in said monitored ventricle, and wherein said impedance measurement unit measures said impedance in said monitored ventricle between said electrode tip and said electrode ring.

11. A monitor as claimed in claim 1 comprising a casing containing said impedance measurement unit, said detector and said comparator, and wherein said impedance measurement unit comprises a unipolar ventricular electrode having an electrode tip adapted for placement in said monitored ventricle, and wherein said impedance measuring unit measures said impedance between said electrode and said casing.

12. A heart stimulator comprising:
a pulse generator adapted to deliver stimulation pulses to a heart of a subject;
an impedance measurement unit including an electrode arrangement adapted to interact with a monitored ventricle of the heart of the subject to measure an impedance in said monitored ventricle for generating an impedance signal corresponding to said impedance;
a detector connected to said impedance measurement unit for detecting an occurrence of a notch in said impedance signal coincident with entry of blood into said monitored ventricle, said detector comprising a differentiator which forms a time derivative of said impedance signal and a loop generator connected to said impedance measurement unit and to said differentiator for plotting impedance values with respect to related time derivative values to form a loop for each cardiac cycle of said heart;
a comparator connected to said loop generator for comparing said loop to a loop template representing a normal loop for the subject, said comparator generating an output indicative of deviations in said loop from normal variations in timing and shape of said notch, thereby obtaining a comparison result; and
a control unit connected to said pulse generator for controlling delivery of said stimulation pulses by said pulse generator dependent on said comparison result.

13. A method for monitoring diastolic relaxation of a ventricle of a heart, comprising the steps of:
   measuring impedance in a monitored ventricle of a heart of a subject, and generating an impedance signal corresponding to said impedance;
   detecting an occurrence of a notch in said impedance signal coincident with entry of blood into said monitored ventricle by forming a time derivative of said impedance signal and plotting impedance values of said impedance signal with respect to related time derivative values to form a loop for each cardiac cycle of the heart; and
   comparing said loop to a loop template representing a normal loop for the subject to identify deviations in said loops from normal variations in timing and shape of said notch.

* * * * *